(12) United States Patent
Lin

(10) Patent No.: US 8,992,761 B2
(45) Date of Patent: Mar. 31, 2015

(54) METHODS FOR PASSIVATING METALLIC IMPLANTABLE MEDICAL DEVICES INCLUDING RADIOPAQUE MARKERS

(75) Inventor: Zhicheng Lin, Palo Alto, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 278 days.

(21) Appl. No.: 13/548,908

(22) Filed: Jul. 13, 2012

(65) Prior Publication Data

US 2014/0014530 A1  Jan. 16, 2014

(51) Int. Cl.
*C25F 3/16* (2006.01)
*A61F 2/86* (2013.01)

(52) U.S. Cl.
CPC ............ *A61F 2/86* (2013.01); *A61F 2240/001* (2013.01); *A61F 2250/0054* (2013.01); *A61F 2250/0098* (2013.01); *C25F 3/16* (2013.01)
USPC ........................................ 205/660

(58) Field of Classification Search
None
See application file for complete search history.

(56) References Cited

U.S. PATENT DOCUMENTS

| | | | |
|---|---|---|---|
| 5,716,400 A | 2/1998 | Davidson | |
| 6,375,826 B1 * | 4/2002 | Wang et al. | 205/684 |
| 6,679,980 B1 * | 1/2004 | Andreacchi | 204/272 |
| 7,357,854 B1 | 4/2008 | Andreacchi | |
| 2007/0173925 A1 | 7/2007 | Fliedner | |
| 2009/0204203 A1 * | 8/2009 | Allen et al. | 623/1.34 |
| 2010/0222866 A1 | 9/2010 | Wachter et al. | |
| 2011/0264161 A1 | 10/2011 | Schiefer et al. | |
| 2012/0016458 A1 * | 1/2012 | Abunassar | 623/1.15 |

FOREIGN PATENT DOCUMENTS

| WO | WO 00/69368 | 11/2000 |
|---|---|---|
| WO | WO 0069368 A2 * | 11/2000 |
| WO | WO 01/61080 | 8/2001 |

OTHER PUBLICATIONS

U.S. Appl. No. 13/271,869, Apr. 1, 2013, Office Action.
U.S. Appl. No. 13/271,869, filed Oct. 12, 2011, Bregulla et al.
U.S. Appl. No. 13/271,869, Apr. 26, 2013, Office Action.
"Forging of Niobium, tantalum, and their alloys," MetalPass, accessed Apr. 18, 2013. http://www.metalpass.com/metaldoc/paper.aspx?docID=312.
U.S. Appl. No. 13/271,869, Nov. 27, 2013, Office Action.
U.S. Appl. No. 13/271,869, Mar. 18, 2014, Notice of Allowance.
U.S. Appl. No. 13/271,869, Jul. 9, 2014, Issue Notification.

* cited by examiner

*Primary Examiner* — Nicholas A Smith
(74) *Attorney, Agent, or Firm* — Workman Nydegger; Jonathan D. Feuchtwang

(57) ABSTRACT

The present disclosure is directed to methods of manufacturing and passivating stents and other implantable medical devices including one or more attached radiopaque markers. In one embodiment, the method includes providing a metallic implantable medical device body without any radiopaque marker(s) attached thereto, primary electropolishing the device body without any markers attached thereto, attaching one or more radiopaque markers to the device body, and lightly electropolishing the device including device body and attached radiopaque markers. Light electropolishing removes no more than about 5 percent by weight of the device (i.e., the device body and attached marker(s)). Light electropolishing passivates the exposed surfaces of the device body and markers, while also providing electropolishing to the region of any welds where the radiopaque marker(s) attach to the device body.

21 Claims, 8 Drawing Sheets

METHODS FOR PASSIVATING METALLIC IMPLANTABLE MEDICAL DEVICES INCLUDING RADIOPAQUE MARKERS

BACKGROUND

The human body includes various lumens, such as blood vessels or other passageways. A lumen may sometimes become at least partially blocked or weakened. For example, a lumen may be at least partially blocked by a tumor, by plaque, or both. An at least partially blocked lumen may be reopened or reinforced with an implantable stent.

A stent is typically a tubular body that is placed in a lumen in the body. A stent may be delivered inside the body by a catheter that supports the stent in a reduced-size configuration as the stent is delivered to a desired deployment site within the body. At the deployment site, the stent may be expanded so that, for example, the stent contacts the walls of the lumen to expand the lumen.

Advancement of the stent through the body may be monitored during deployment. After the stent is delivered to the target site, the stent can be monitored to determine whether the placement thereof is correct and/or the stent is functioning properly. Methods of tracking and monitoring stent after delivery include X-ray fluoroscopy and magnetic resonance imaging ("MRI").

Some stents or portions thereof are formed of materials exhibiting super-elastic characteristics (e.g., nickel-titanium), which can be particularly beneficial in expanding the stent. One distinct disadvantage of some such stent materials though, is their relatively limited radiopacity. An intracorporeal device, such as a stent, and its delivery system should be radiopaque or fluoroscopically visible to allow the practitioner to visualize position and orientation of the device and delivery system in real time. This is important in tracking delivery of the device and delivery system through the patient's vasculature to the precise desired location. The degree of radiopacity and fluoroscopic visibility depends on the device being more absorptive of x-rays than the surrounding tissue. A greater difference in x-ray absorption thus provides better contrast between the device and the surrounding tissue, and thus better resolution and information as to position and orientation of the device as it is delivered.

Many super-elastic alloy materials, such as nickel-titanium, as well as many other materials employed in stent manufacture, for example, stainless steel and even some cobalt-chromium alloys exhibit less radiopacity than would be desirable.

Radiopacity may be improved by increasing stent wall thickness (e.g., strut thickness) although this detrimentally affects the flexibility of the stent, which flexibility is needed for ease of delivery. In addition, increasing the stent wall thickness may not be acceptable from a practical perspective, as there may simply not be additional space available where the stent is to be delivered within the intended vasculature. One method for increasing fluoroscopic visibility and radiopacity of such stents is to attach one or more radiopaque markers to the stent and/or delivery system.

Despite a number of different approaches for increasing radiopacity, manufacturers and users of stents continue to seek improved stent designs and processing techniques.

SUMMARY

The present disclosure is directed to a method of manufacturing implantable medical devices including one or more radiopaque markers. The method includes providing a metallic implantable medical device body without any radiopaque markers attached thereto, primary electropolishing the metallic implantable medical device body, attaching one or more metallic radiopaque markers to the device body, and lightly electropolishing the device body after the one or more attached radiopaque markers are attached. The radiopaque markers comprise a metal that is different from that of the device body, and the light electropolishing may remove no more than about 5% by weight of the device body with attached marker(s). The light electropolishing performed after attachment of the radiopaque marker(s) passivates the exterior surface of the implantable medical device body, as well as the exterior surface of the attached radiopaque marker(s). In addition, it provides polishing of the weld interface where the radiopaque marker(s) attaches to the device body. The light electropolishing also optimizes the surface finish of the device so as to provide better control during catheter deployment.

In an embodiment, the light electropolishing may be achieved through use of a single electrolyte solution that is suitable for electropolishing of both the metal of the device body and that of the radiopaque marker(s). In such an embodiment, the light electropolishing is accomplished by immersing the implantable medical device body with attached radiopaque marker(s) into an electrolyte solution that is capable of electropolishing both the metal of the implantable medical device body, as well as the different metal of the attached radiopaque marker(s). The immersed implantable medical device body and radiopaque marker(s) are subjected to an applied electrical current, whereby metal atoms from the stent body and radiopaque marker(s) are stripped away. Due to gases present within the electrolyte solution or generated therein by the electropolishing process, a passivation layer is substantially simultaneously formed over the exterior surfaces of both the device body and radiopaque marker(s), including the weld interface.

In another embodiment, the light electropolishing is accomplished in a two step process in which the device body with attached radiopaque marker(s) is immersed into a first electrolyte solution that is capable of electropolishing the metal of the device body while subjecting the device to an applied electrical current. The device is also immersed into a second, different electrolyte solution that is capable of electropolishing the metal of the attached radiopaque marker(s) while subjecting the immersed device to an applied electrical current. Thus, processing in the first electrolyte solution provides light electropolishing of the device body, while processing in the second electrolyte solution provides light electropolishing of the attached radiopaque marker(s).

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

To further clarify at least some of the advantages and features of the present disclosure, a more particular description of the disclosure will be rendered by reference to various embodiments thereof that are illustrated in the appended drawings. It is appreciated that these drawings depict only various embodiments of the disclosure and are therefore not to be considered limiting of its scope. The various embodiments will be described and explained with additional specificity and detail through the use of the accompanying drawings in which.

DETAILED DESCRIPTION

I. Introduction

The present disclosure is directed to methods of manufacturing and passivating implantable medical devices including one or more radiopaque markers. The method includes providing a metallic implantable medical device body that does not include radiopaque markers attached thereto, primary electropolishing the implantable medical device body to achieve a desired surface smoothness, attaching one or more metallic radiopaque markers to the implantable medical device body, and lightly electropolishing the implantable medical device body and radiopaque marker(s) once the marker(s) are attached. The light electropolishing may remove no more than about 5 percent by weight of the implantable medical device body and radiopaque marker(s). The radiopaque markers comprise a metal that is different from that of the metallic implantable medical device body to which the marker(s) are attached, and the light electropolishing acts to electropolish and passivate an exterior surface of the implantable medical device body with attached radiopaque marker(s), including the weld or other attachment joint between the device body and radiopaque marker(s).

II. Example Stents

Figure 1A:
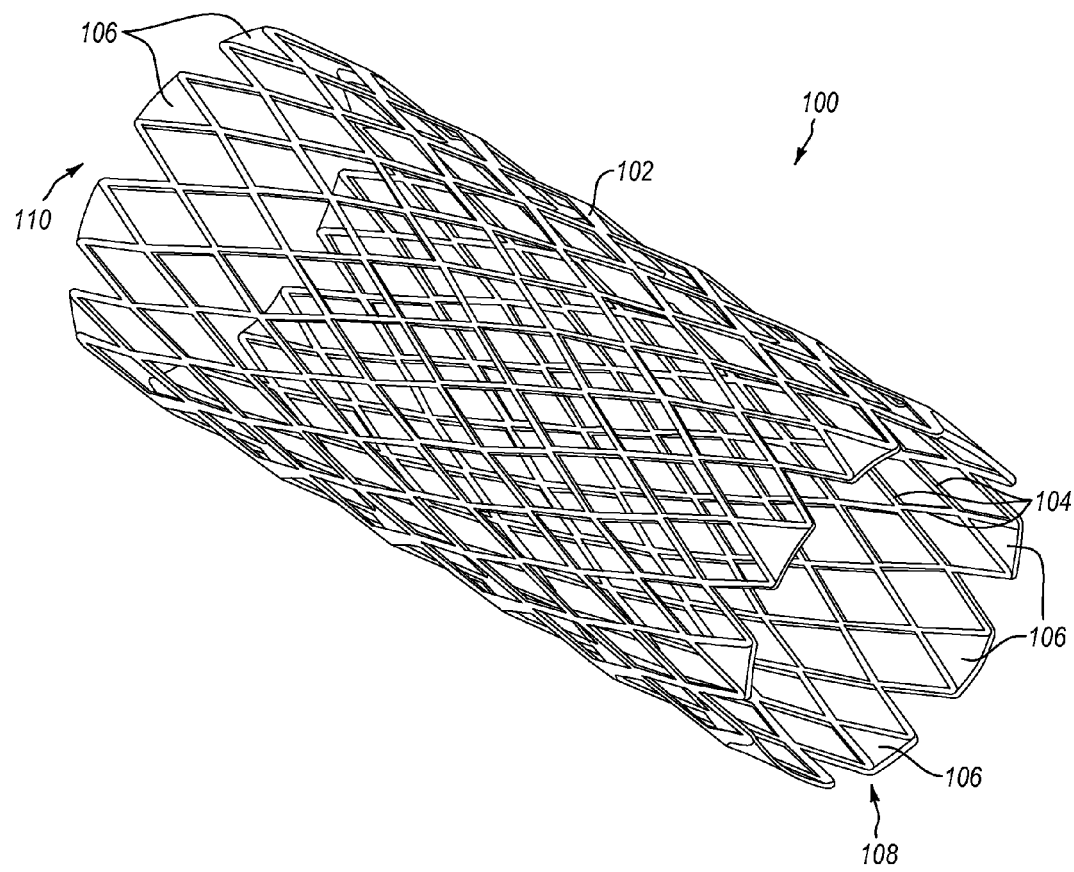
FIG. 1A is an isometric view of a stent including attached radiopaque markers made according to an embodiment of the present disclosure.

The present manufacture and passivation methods may be employed with respect to any desired implantable medical device. In an embodiment, the implantable medical device is a stent. FIG. 1A is an isometric view of a stent 100 made according to an embodiment of the present disclosure. The stent 100 includes a stent body 102 sized and configured to be implanted and deployed into a lumen of a living subject. The stent body 102 may be defined by a plurality of interconnected struts 104 configured to allow the stent body 102 to radially expand and contract. However, it is noted that the illustrated configuration for the stent body 102 is merely one of many possible configurations, and other stent-body configurations are encompassed by the present disclosure. For example, the struts 104 may be integrally formed with each other as shown in the illustrated embodiment, separate struts may be joined together by, for example, welding or other joining process, or separate stent sections may be joined together. Any stent body configuration apparent to those of skill in the art may be employed.

In order to provide sufficient radiopacity to be visible in X-ray fluoroscopy and MRI, stent 100 includes one or more radiopaque markers 106 attached to stent body 102. In an embodiment, one or more markers 106 may be attached (e.g., laser welded) to struts 104 adjacent first and second ends 108, 110 of stent 100. The radiopaque marker(s) 106 comprise a material different from that of the other portions of stent 100, so as to provide higher radiopacity. For example, radiopaque marker(s) 106 may typically comprise a material having greater radiopacity than the material of stent body 102. In an embodiment, stent body 102 may comprise a nickel-titanium alloy (e.g., NITINOL), while the radiopaque markers 106 may comprise tantalum, platinum, palladium, gold, or combinations thereof. Of course, other materials may be employed for the stent body 102 and radiopaque markers 106.

Stent body 102 may be formed by any suitable process. For example, a solid-walled tube may be cut (e.g., laser cut, electro-discharge machining) to define struts 104. Alternatively, any other suitable process may be employed, e.g., a drawn wire may be formed into a tubular stent structure by one or more of knitting, coiling, weaving, or welding one or more of such wires. In another alternative, sheet metal may be etched (e.g., chemically etched or laser cut) to provide the desired stent pattern. The sheet metal may be folded and joined (e.g., through laser welding or through mechanical interlock of respective folded ends) to form a desired tubular configuration.

Referring still to FIG. 1A, for example, an average thickness of the struts 104 of stent body 102 may be selected so as to reduce vessel injury and enhance deliverability while providing the necessary strength and other characteristics. In an embodiment, the strut thickness in a radial direction may be about 25 μm to about 350 μm. The thinner thickness dimensions (e.g., about 25 μm) might be more typical of a neuro stent, while the thicker dimensions (e.g., about 350 μm) may be more typical of an aorta stent. Other intermediate thickness dimensions may be from about 40 μm to about 100 μm, about 60 μm to about 80 μm (e.g., about 70 μm), or about 50 μm to about 90 μm.

In some embodiments, the stent body 102 may be etched or descaled in an acid (e.g., hydrofluoric acid) to remove features (e.g., slag, remelt, heat-affected zones, etc.) associated with forming the struts 104 via laser cutting. Any such descaling may occur prior to primary electropolishing. In addition, the stent body, the radiopaque marker(s), or both may be heat treated as desired (e.g., to relieve stress or to alter the metal crystal structure).

Figure 1B:
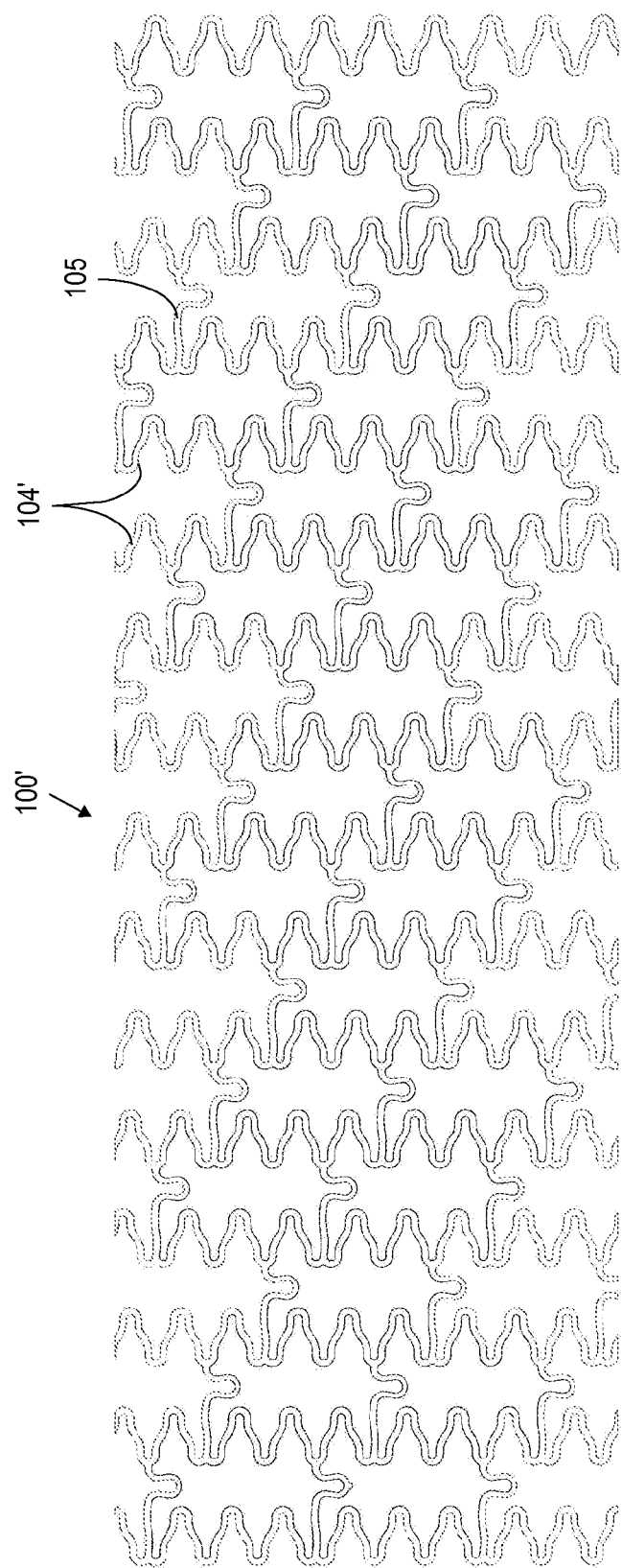
FIG. 1B illustrates another strut design for a stent according to an embodiment of the present disclosure.

FIG. 1B illustrates a strut design for another stent 100' including a number of interconnected struts 104' and connector elements 105 that connect adjacent struts 104. The stent 100' can be sized and configured to be implanted and deployed into a lumen of a living subject. However, it is noted that the illustrated configurations for the strut design of stent 100, and that of stent 100' are merely two of many possible configurations, and other stent-body configurations are encompassed by the present disclosure. As with stent 100 of FIG. 1A, radiopaque marker(s) may be attached to struts 104', connector elements 105, or both.

Other implantable medical devices besides stents that include attached radiopaque marker(s) may benefit from the disclosed methods by which primary electropolishing of the implantable structure is first accomplished without any radiopaque markers attached thereto, followed by light electropolishing of the structure after attachment of the radiopaque marker(s). For example, other such implantable medical devices may include, but are not limited to, guide wires, closure elements (e.g., staples), pacemaker leads, orthopedic devices, embolic coils, sutures, prosthetic heart valves, mitral valve repair coils, filters, or other medical devices or portions thereof for deploying the foregoing medical devices.

III. Example of Stent Deployment

Implantable medical devices disclosed herein, such as the stent 100 shown in FIG. 1A, may be delivered into a body of a living subject by a number of different techniques. For example, a delivery catheter may be employed to deliver and deploy the stent 100. An embodiment of a method for delivering a stent into a body lumen of a living subject may include: (1) providing a stent as disclosed herein; (2) delivering the stent to a desired deployment site within the body lumen of the living subject; (3) expanding the stent so that it applies a radially outward force to an inner wall of the body lumen.

Figure 2:
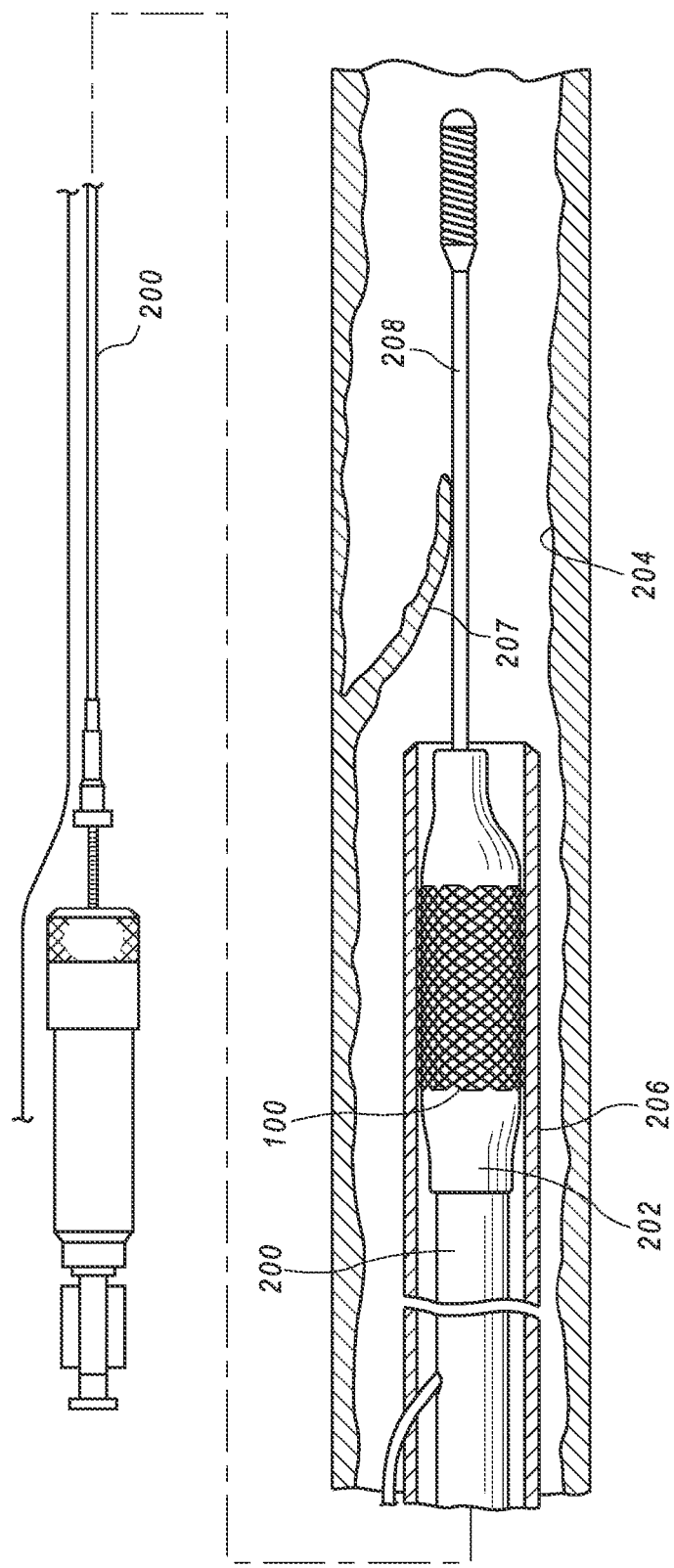
FIG. 2 is a side elevation view, in partial cross-section, of a delivery catheter within a body lumen having a stent made according to an embodiment of the present disclosure disposed about the delivery catheter.

FIG. 2 is a side elevation view, in partial cross-section, of a delivery catheter 200 having a stent 100 disposed thereabout according to an embodiment of the present disclosure, which provides an example of the manner in which stent 100 may be inserted and deployed within a living subject. Delivery catheter 200 has an expandable member or balloon 202 for expanding stent 100, on which stent 100 is mounted, within a body lumen 204 such as an artery. For example, body lumen 204, as shown in FIG. 2, may have a dissected lining 207 that has occluded a portion of body lumen 204.

Delivery catheter 200 may be a conventional balloon dilatation catheter commonly used for angioplasty procedures. In use, stent 100 may be mounted onto inflatable balloon 202 on the distal extremity of delivery catheter 200. Balloon 202 may be slightly inflated to secure stent 100 onto an exterior of balloon 202. The catheter/stent assembly may be introduced within a living subject using a conventional Seldinger technique through a guiding catheter 206. Guide wire 208 may be disposed across the damaged arterial section with detached or dissected lining 207 and then the catheter/stent assembly may be advanced over guide wire 208 within body lumen 204 until stent 100 is directly under detached lining 207. For example, guide wire 208 may be made from a super-elastic nickel-titanium alloy (e.g., NITINOL), or another suitable material. Balloon 202 of catheter 200 may be expanded, expanding stent 100 against the interior surface defining body lumen 204 by, for example, permanent plastic deformation of stent 100. When deployed, stent 100 holds body lumen 204 open after catheter 200 and balloon 202 are withdrawn.

IV. Embodiments of Methods of Stent or Other Implantable Medical Device Manufacture and Passivation In an embodiment, the present methods may achieve passivation of the stent body, as well as the radiopaque markers, through use of electropolishing, rather than a traditional chemical passivation technique. For example, while electropolishing does serve to remove metal material from the structure being electropolished, it also results in the formation of a thin passivation film layer (e.g., an oxide of the underlying metal) at the surface of the structure. According to an embodiment, electropolishing is achieved by immersing the structure to be electropolished into an electrolyte solution, and subjecting the immersed structure to an applied electrical current, resulting in anodic metal dissolution of metal on the surface of the structure.

Figure 3:
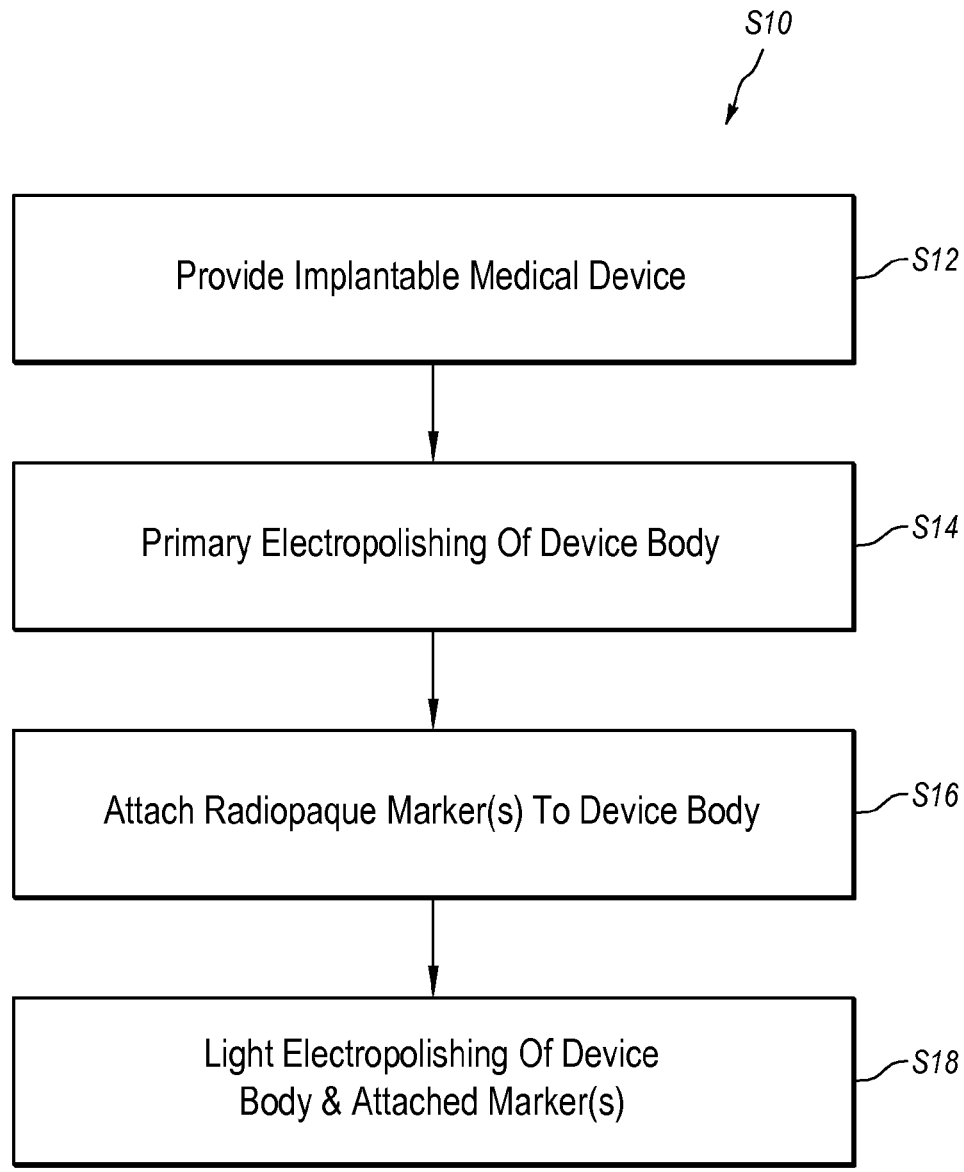
FIG. 3 is a flow chart illustrating a method for making and passivating an implantable medical device body including one or more radiopaque markers according to an embodiment.

As shown in FIG. 3, according to method S10, an implantable medical device, such as a tubular stent body is provided at S12. Primary electropolishing (S14) of the device body prior to attachment of the radiopaque marker(s) smooths the surface through removal of sharp edges and points, to achieve a desired surface smoothness and a size near the desired final dimensions. Once the stent body has been polished so as to achieve the desired surface smoothness and near final dimensions desired, the radiopaque marker(s) are attached, as indicated at S16. Finally, light electropolishing (S18) of the device body and attached radiopaque marker(s) is performed, removing no more than about 5 percent by weight of the structure, and providing passivation of the exterior surface of the device body and attached radiopaque marker(s).

The implantable medical device body may be prepared by any suitable technique, such as by laser cutting. Additional treatments prior to primary electropolishing may include descaling in order to remove slag and remelt, and to treat heat-affected zones. Descaling may also serve to at least partially remove undesirable features such as burrs and sharp edges. Any remaining portions of such burrs and sharp edges may be fully removed during primary electropolishing.

Figure 4:
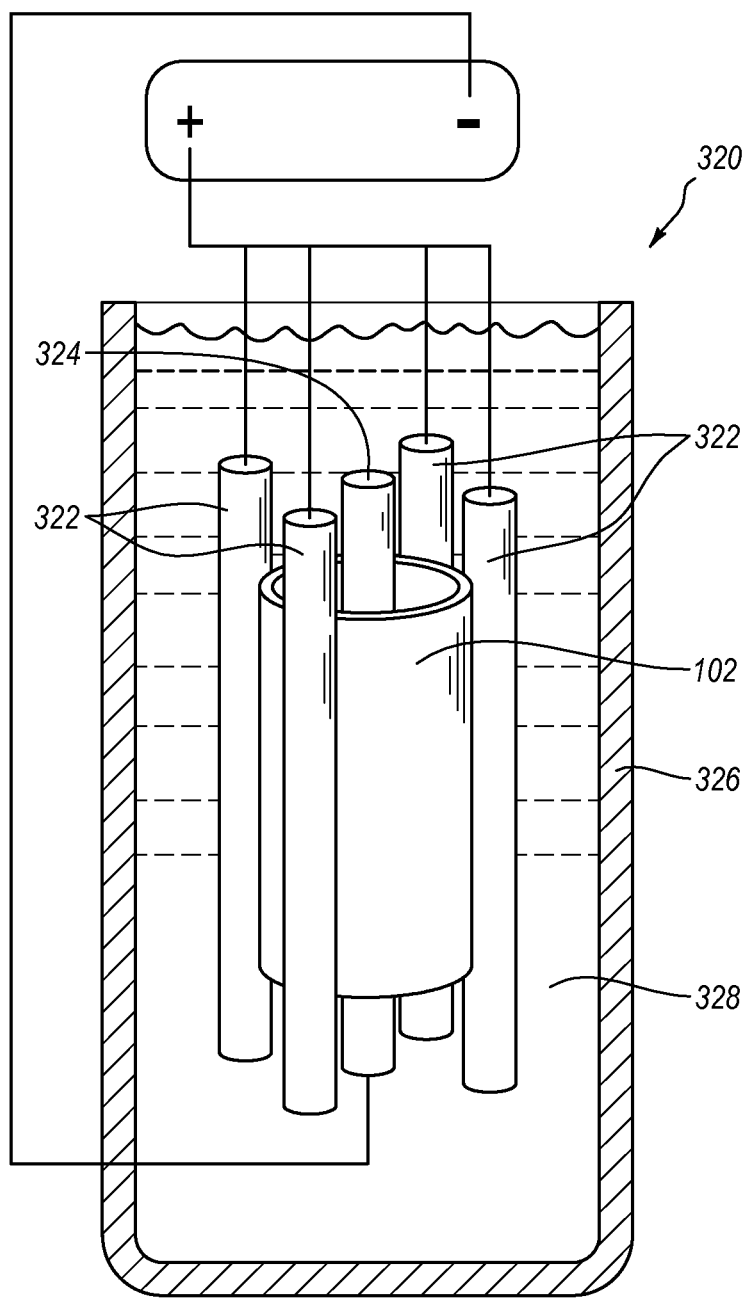
FIG. 4 is a side elevation view, in partial cross-section, of an example electropolishing fixture in an electrolyte bath that may be used for practicing embodiments of methods disclosed herein.

Primary electropolishing may serve to provide a fine uniform polish on both the interior and exterior surfaces of the metallic stent body or other implantable device body. One or more stent or other implantable device bodies may be placed within an electropolishing fixture and immersed into an electrolyte bath while an electrical current is applied between an anode and a cathode of the fixture. FIG. 4 shows a stent body 102 within an example fixture 320. Fixture 320 includes a plurality of anodes 322 arranged about the exterior of stent body 302, with a center cathode 324 positioned within the center interior of stent body 302. In an embodiment, anodes 322 are equally spaced about the perimeter of stent body 302 so as to maintain a substantially uniform electric field density between stent body 302 and center cathode 324. Electropolishing fixture 320 is placed within container 326 filled with the electrolyte bath 328.

Anodes 322 are electrically connected to positive terminal 330, while cathode 324 is electrically connected to negative terminal 332 of a power supply. When electrical current is applied, current flows from anodes 322, through electrolyte solution 328 and stent body 302, to cathode 324. As current flows, atoms of metal from stent body 302 are removed, migrating to cathode 324. Because protrusions are removed faster than material from depressions or a smooth surface, a polishing effect is achieved so that the surface smoothness of the stent body increases. For example, a surface finish of about 0.2 micron to about 0.05 micron surface roughness may be desirable, and achieved in primary electropolishing.

Because stent body 302 may contact holding anodes 322, the stent body may be rotated one or more times during primary electropolishing. For example, stent body 302 may be electropolished for a given period of time, rotated about 120° about its longitudinal axis, electropolished for the same given period of time, rotated another about 120°, and electropolished for the same given period of time. In another embodiment, the electropolishing times associated with each rotation may differ. The stent body may then be removed from fixture 320, flipped 180° relative to its longitudinal axis, and electropolished three more times, rotating the stent body 120° between electropolishing periods.

Polishing cycle time depends on the electrolyte bath employed, the size of the stent, and field density between the stent and the cathode(s). Field density itself is dependent on the amount of current applied to the anode(s), the stent, and cathode(s). Current flow depends on resistivity of the anode, stent, and cathode materials, and the voltage applied to the circuit. As such, it will be understood that various aspects of the electropolishing fixture 320, electrolyte bath 328, and stent body 302 may be adjusted, which may affect electropolishing cycle times, applied voltage, current, and other parameters.

In any case, primary electropolishing of stent body 302, prior to attachment of any radiopaque marker(s), may result in removal of about 15 percent to about 30 percent of stent body 302 by weight. More particularly, primary electropolishing may remove about 20 percent to about 30 percent of stent body by weight. In an embodiment, primary electropolishing removes at least about 15 percent of stent body 302 by weight. As a result of primary electropolishing, a desired surface finish of about 0.2 micron to about 0.05 micron surface roughness is achieved. Surface roughness and recognition of when target thickness/mass removal values have been reached may be monitored through optical measurements, weight measurements, or both.

As indicated by FIG. 3, once stent body 302 has been subjected to primary electropolishing so as to achieve the desired strut thickness and surface finish, one or more radiopaque markers are attached to stent body 302. As shown in FIG. 1A, the radiopaque marker(s) may be attached at or near one or more of the first and second ends 108, 110 of stent 100. Radiopaque marker(s) 106 may be attached by any suitable method. In an embodiment, the marker(s) 106 are attached by laser welding. Other suitable attachment processes may alternatively be employed.

Rather than subjecting the stent body including attached radiopaque marker(s) to a chemical passivation process, the stent 100 is lightly electropolished, where the electropolishing parameters (e.g., particularly cycle time) are selected so that no more than about 5 percent by weight of stent 100 (i.e., including both stent body 102 and marker(s) 106) is removed. Rather than material removal, the principal purpose of light electropolishing is to form a passivation layer over the exposed metal surfaces of both stent body 102 and marker(s) 106. While a passivation layer may have formed over the exposed surface of stent body 102 during primary electropolishing, such a passivation layer may have been disrupted as a result of attaching marker(s) 106, e.g., as a result of heat generated by laser welding. The passivation layer may typically be an oxide of the underlying metal material, having a thin film surface thickness of less than about 200 Å, from about 50 Å to about 200 Å, or about 100 Å.

In addition, radiopaque marker(s) 106 may not include a passivation layer prior to attachment, and even where they did include a passivation layer, it may have been disrupted by attachment by laser welding. Furthermore, subjection to light electropolishing provides a smoothing, polishing treatment to the weld interfaces where radiopaque marker(s) 106 are attached to stent body 102, which welds may have not received any prior polishing.

Thus, light electropolishing of stent 100 including stent body 102 and attached radiopaque marker(s) 106 serves to ensure that a passivation layer is formed over the entire exposed surface of stent 100, while also providing polishing of the welds attaching marker(s) 106 to stent body 102. Because stent body 102 comprises a different metal material than that of radiopaque marker(s) 106, it might be expected that any attempt to electropolish such a structure including two dissimilar metals might result in pitting adjacent the weld interface of the two metal materials, as one metal is preferentially dissolved relative to the other. The fact that no such pitting has been observed to occur by the present inventor is surprising and unexpected. Furthermore, the ability to thus lightly electropolish the stent including two dissimilar metal materials in order to form a passivation layer, while also providing a polishing treatment to the region of the attachment welds is highly advantageous.

The laser or other formed welds of existing stents including radiopaque markers are not polished, but rather may only be passivated chemically. This not only results in a significantly higher surface roughness in the region of the weld, but results in biocompatibility problems. In other words, the regions of the welds are substantially more vulnerable to biocompatibility problems as a result of their not being polished. By lightly electropolishing the stent body with attached radiopaque marker(s) after attachment of the marker(s), not only is the region of the weld fully passivated, but it also is polished as a result of the light electropolishing.

In an embodiment, stent body 102 comprises a nickel-titanium alloy (e.g., NITINOL or NITINOL modified by replacement of at least a portion of the nickel with platinum), a cobalt chromium alloy (e.g., including, but not limited to L-605 or MP-35N), stainless steel, or a stainless steel alloy modified through the addition of platinum or another radiopaque metal (e.g., a platinum group metal). Of course, other biocompatible metals or alloys may similarly be employed.

In an embodiment, radiopaque marker(s) 106 comprise a material having a higher radiopacity than the material of stent body 102. Radiopaque marker(s) 106 may comprise tantalum, a tantalum alloy, a nickel-titanium-platinum alloy, gold, a gold alloy, platinum, a platinum-uranium alloy, another platinum alloy, palladium, a palladium alloy, or other suitable biocompatible metallic material having greater radiopacity than the material of stent body 102. In one embodiment, the stent body comprises nickel-titanium, while the radiopaque marker(s) comprise tantalum (e.g., a tantalum alloy). One such tantalum alloy may include about 80% tantalum, about 10% niobium, and about 10% tungsten. Such alloys are described in U.S. patent application Ser. No. 13/271,869, entitled HEAT-TREATED TANTALUM-ALLOY PRODUCTS, IMPLANTABLE MEDICAL DEVICES INCORPORATING SAME, AND METHODS OF PROCESSING TANTALUM-ALLOY, herein incorporated by reference in its entirety.

In some embodiments, light electropolishing of both the material of stent body 102 and that of radiopaque marker(s) 106 is performed substantially simultaneously. For example, an electropolishing fixture such as that shown in FIG. 4 and described in further detail in U.S. Pat. No. 6,375,826 may be suitable for use in simultaneously lightly electropolishing stent body 102 and marker(s) 106. By way of example, a stent including a nickel-titanium stent body 102 and tantalum marker(s) 106 may be lightly electropolished by such a simultaneous method using an electrolyte bath including methanol, hydrochloric acid, and sulfuric acid. The electrolyte bath may initially be void of water, although water may form during the electropolishing process as a result of generation of discharge gases. In one embodiment, the electrolyte bath may comprise about 70% to about 95% by weight methanol, about 5% to about 15% sulfuric acid, and about 1% to about 6% hydrochloric acid (e.g., about 90% methanol, about 4% hydrochloric acid, and about 6% sulfuric acid). Additional details of exemplary suitable electropolishing baths are disclosed in U.S. Pat. No. 6,375,826, herein incorporated by reference in its entirety. Such electropolishing baths may be suitable for both primary and light electropolishing.

As mentioned above, cycle time depends on various factors, particularly applied current. In one embodiment, cycle time may be from about 5 seconds to about 20 seconds, or about 10 seconds to about 20 seconds (e.g., about 10 seconds to about 15 seconds) per rotation position. Total light electropolishing time (including all cycle times for each rotation) may be from about 10 seconds to about 1 minute. Because light electropolishing is intended to remove no more than about 5% of the stent by weight, total number of rotations, and thus total electropolishing time, is typically shorter than electropolishing times employed during primary electropolishing. For example, the stent 100 may be rotated a single time (i.e., 2 electropolishing cycles), after which it is removed. By way of comparison, primary electropolishing may include substantially more rotations (e.g., 6 rotation positions). Cycle times for primary and light electropolishing may be within similar ranges, although less cycles will typically be employed during light electropolishing in order to maintain material removal to no more than about 5% of the stent.

For example total primary electropolishing time may be from about 30 seconds to about 4 minutes, while individual primary electropolishing cycle times may be from about 5 seconds to about 20 seconds (e.g., about 6 to about 10 rotations may occur during primary electropolishing).

Applied current density employed during both primary electropolishing and light electropolishing may be from about 300 Amps/ft$^2$ and about 900 Amps/ft$^2$, from about 400 Amps/ft$^2$ and about 800 Amps/ft$^2$, or about 500 Amps/ft$^2$. In an embodiment, total light electropolishing time may be about 10 seconds to about 1 minute, while applying a current density of about 400 Amps/ft$^2$ and about 800 Amps/ft$^2$. One or two rotations may be employed after a cycle time of about 5 seconds to about 20 seconds (e.g., 10-40 seconds total light electropolishing time).

In an embodiment, cleaning and drying processes may be employed between electropolishing cycles to provide a new diffusion layer for further improved electropolishing results.

In another embodiment, depending on the particular materials employed for stent body 102, marker(s) 106, and electrolyte bath 328, the light electropolishing of stent body 102 and marker(s) 106 may proceed separately. In other words, one or both of the electrolyte bath and the electropolishing fixture may be particularly configured to lightly electropolish the stent body 102, while the electrolyte bath and/or electropolishing fixture employed to lightly electropolish the radiopaque marker(s) 106 may be differently configured for its particular purpose. For example, the fixture may position the anode(s) and cathode(s) in close proximity to the stent body 102, but away from the radiopaque marker(s) 106 so that the electric field density is weak relative to the radiopaque marker(s) 106, so that electropolishing occurs substantially within one region of the stent, but not the other. In addition, the electrolyte bath composition may be specifically tailored for electropolishing the stent body, rather than the metallic material of marker(s) 106.

Figure 5A:
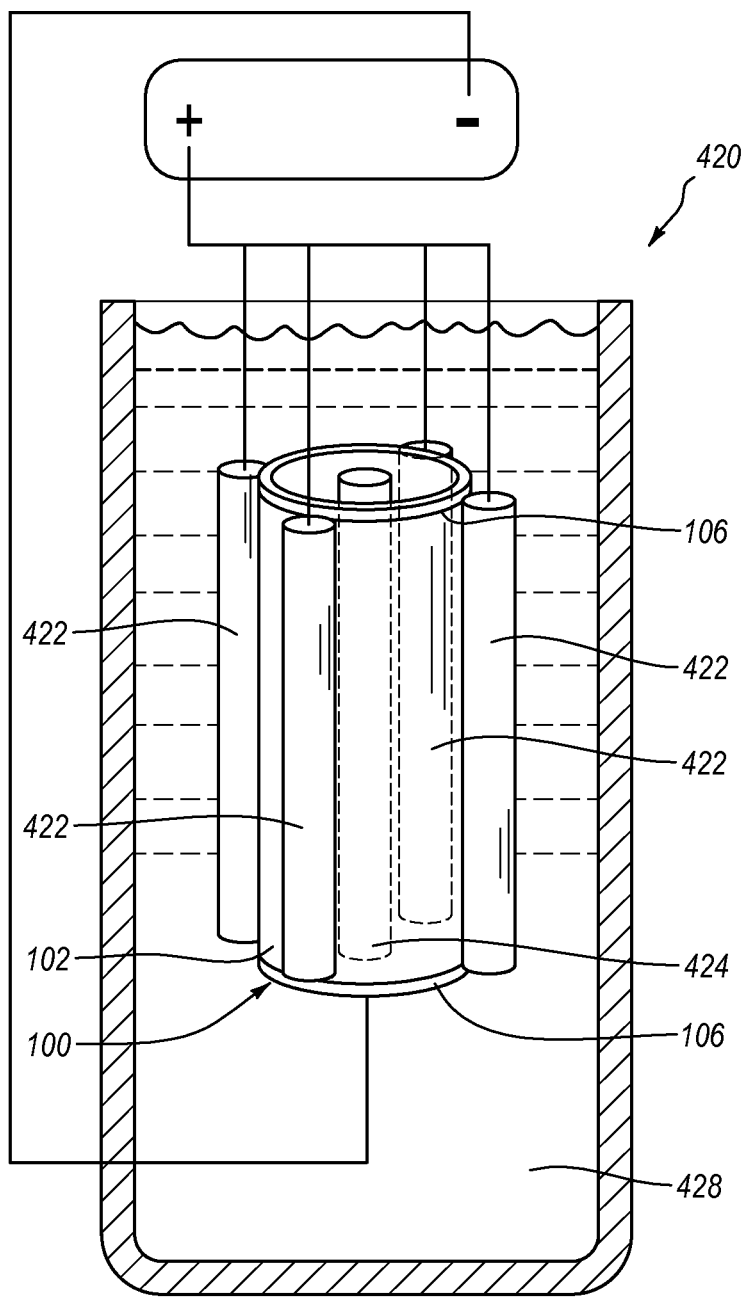
FIG. 5A is a side elevation view, in partial cross-section, of an electropolishing configuration that may be employed as a first electropolishing step of a two-step light electropolishing method in which the stent body and the attached radiopaque marker(s) are electropolished in separate steps.
Figure 5B:
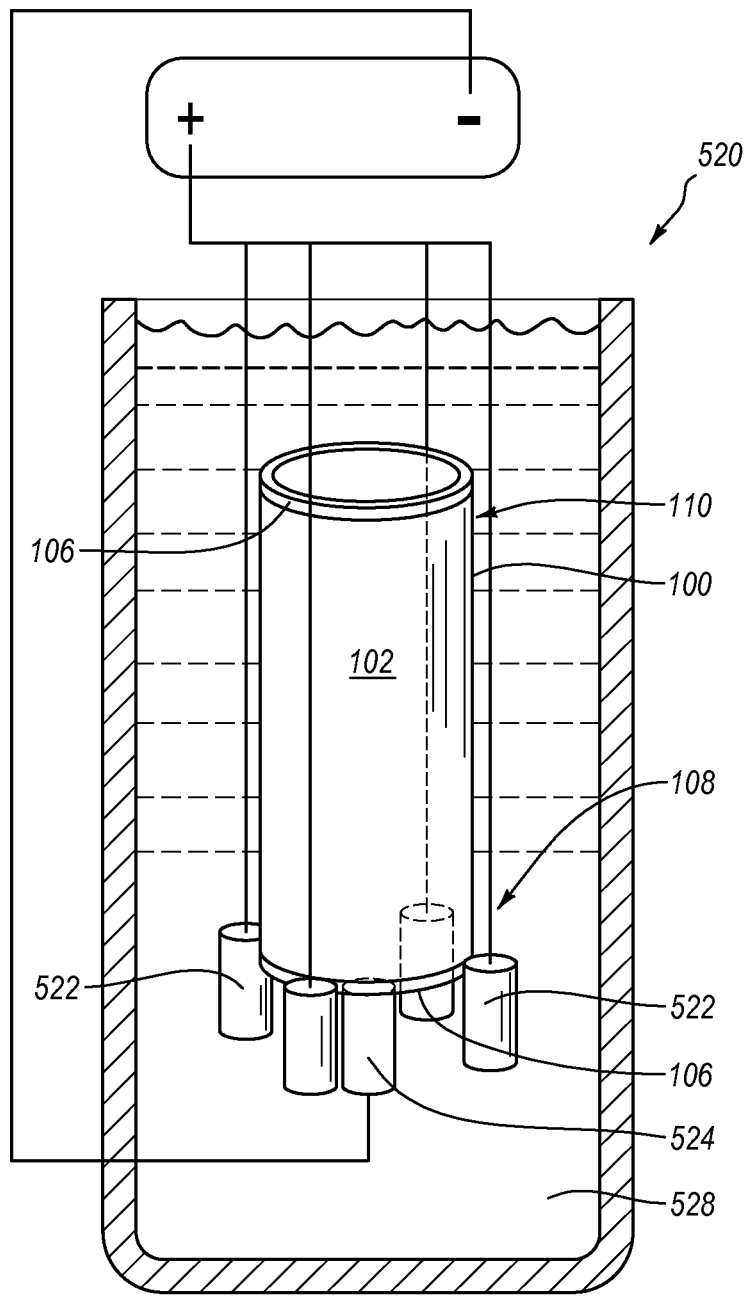
FIG. 5B is a side elevation view, in partial cross-section, of an electropolishing configuration that may be employed as a second electropolishing step of a two-step light electropolishing method in which the stent body and the attached radiopaque marker(s) are electropolished in separate steps.
Figure 5C:
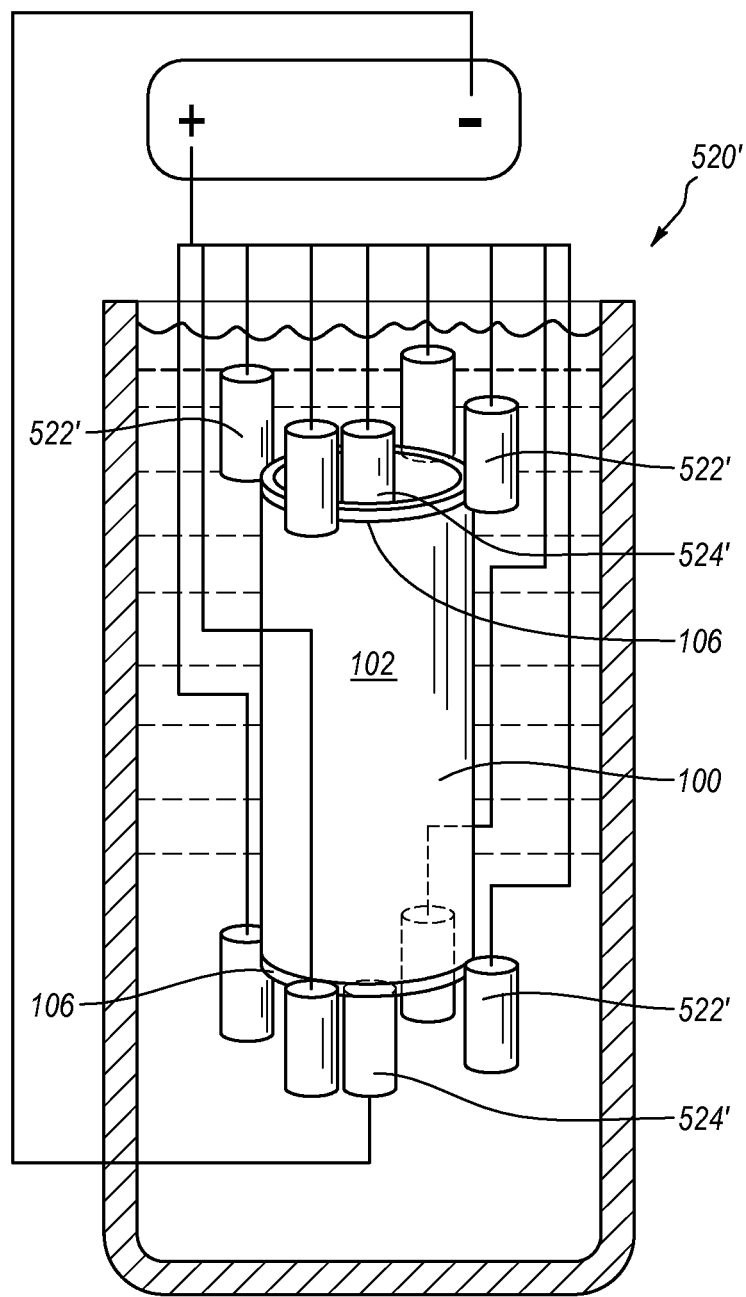
FIG. 5C is a side elevation view, in partial cross-section, of an alternative electropolishing configuration that may be employed as a second electropolishing step of a two-step light electropolishing method in which the stent body and the attached radiopaque marker(s) are electropolished in separate steps.

FIGS. 5A-5C illustrate non-limiting examples of electropolishing fixtures by which such a non-simultaneous light electropolishing procedure may be accomplished. FIG. 5A shows an electropolishing fixture 420 similar to that shown in FIG. 4, but in which anodes 422 are shortened so as to be of a length that positions the anodes 422 adjacent stent body 102, but that anodes 422 terminate before extending adjacent to radiopaque marker(s) 106. Similarly, cathode 424 is configured to extend adjacent the full length of stent body 102, but to terminate short of radiopaque marker(s) 106. In addition, electrolyte bath 428 may be specifically tailored so as to electropolish the metal material of stent body 102, rather than the metal material of marker(s) 106.

FIGS. 5B and 5C show example electropolishing fixtures for targeted electropolishing of radiopaque marker(s) 106, while minimizing electropolishing of stent body 102. FIG. 5B shows a fixture 520 including anodes 522 and cathode 524 configured to be positioned adjacent to first end 108 of stent 100 that includes marker(s) 106. Because electrodes 522 and 524 are positioned near markers 106, but away from stent body 102, electropolishing is preferentially targeted towards marker(s) 106. Electrolyte bath 528 may similarly be specifically tailored so as to target electropolishing of marker(s) 106, while minimizing electropolishing of stent body 102. Once marker(s) 106 at first end 108 are lightly electropolished as desired, stent 100 may be flipped 180° about its longitudinal axis, and light electropolishing of radiopaque marker(s) 106 disposed at proximal end 110 may then be lightly electropolished.

In embodiments where one or more of the markers 106 are disposed along the central portion of stent 100, electrodes 522 and 524 may be moved axially to be disposed near the central location of the marker(s).

FIG. 5C illustrates a fixture 520' that is similar to fixture 520, but in which anodes 522' and cathodes 524' are included adjacent both ends 108 and 110 of stent 100 so as to position the electrodes near markers 106, but away from stent body 102. In this way, markers 106 at both first and second ends 108 and 110 of stent 100 may be lightly electropolished simultaneously, without any need to flip stent 100 180° mid-way through light electropolishing.

In the embodiments shown in FIGS. 5A-5C, any tendency for the dissimilar metals of the markers and stent body to exhibit pitting as a result of differences in galvanic potentials of the respective metals may be minimized or prevented by focusing the light electropolishing current density to the area where the marker(s) are disposed. For example, configurations such as those described above, or a movable cathode ring (e.g., rather than a cylinder) that covers the entire stent length may be employed to limit current density exposure of the other portions of the stent body.

In an embodiment, the container holding the electrolyte may comprise metal (e.g., stainless steel). In such an embodiment, the cathode may be electrically connected to the container. Where employed, such features may provide improved electropolishing and light electropolishing.

Various electrolyte bath compositions may be employed. For example, where electropolishing stainless steel or similar materials (e.g., a platinum modified stainless steel), a suitable electrolyte bath may include about 50% to about 75% acid(s), about 5% to about 15% deionized water, and one or more inhibitors. Examples of suitable acids include hydrochloric acid, sulfuric acid, hydrofluoric acid, phosphoric acid, and combinations thereof. In an embodiment, the electrolyte solution employed in the electropolishing may be an inaqueous (i.e., initially substantially void of water) acidic solution. For example, the electrolyte solution may contain methanol (or another alcohol), sulfuric acid, methanolic hydrochloric acid (methanol HCl) and, optionally, a desiccating agent such as polyethylene glycol ("PEG") and/or ethylene glycol. In another example, the electrolyte solution may contain methanol, sulfuric acid, and ethylene glycol. In a specific embodiment, the sulfuric acid concentration in the electrolyte solution is about 1.5 molar ("M") to about 3 M (e.g., about 1.9 M), and the ethylene glycol concentration is about 0.8 M to about 1.1 M (e.g., about 0.9 M). Alternative electrolyte bath compositions including a major fraction of methanol (e.g., 70% or more) and a small fraction of acid(s) are described above. As will be apparent in light of the present disclosure, selection of electrolyte bath formulations depends at least in part of the target metal to be electropolished.

The embodiments of the present disclosure may be embodied in other specific forms without departing from its spirit or essential characteristics. The described embodiments are to be considered in all respects only as illustrative and not restrictive. Therefore, the scope of the disclosure is indicated by the appended claims rather than by the foregoing description. All changes that come within the meaning and range of equivalency of the claims are to be embraced within their scope.

The invention claimed is:

1. A method of manufacturing and passivating an implantable medical device including one or more radiopaque markers, the method comprising:
   providing a metallic implantable medical device body without any radiopaque markers attached thereto;
   primary electropolishing the implantable medical device body;
   attaching one or more metallic radiopaque markers to the implantable medical device body, the one or more radiopaque markers comprising a metal that is different from that of the metallic implantable medical device body; and
   lightly electropolishing the implantable medical device body with one or more attached radiopaque markers, the light electropolishing removing no more than about 5 percent by weight of the implantable medical device body including the one or more attached radiopaque markers;
   wherein the light electropolishing of the implantable medical device body with one or more attached radiopaque markers passivates an exposed surface of the implantable medical device including the implantable medical device body and the one or more attached radiopaque markers.

2. The method of claim 1 wherein the metallic implantable medical device body comprises a material selected from the group consisting of a nickel-titanium alloy, a cobalt-chromium alloy, stainless steel, a platinum modified stainless steel, and combinations thereof.

3. The method of claim 1 wherein the one or more attached metallic radiopaque markers comprise a material selected from the group consisting of tantalum, gold, a platinum-uranium alloy, a platinum modified stainless steel, and combinations thereof.

4. The method of claim 1 wherein the metallic implantable medical device body comprises a nickel-titanium alloy.

5. The method of claim 4 wherein the one or more attached metallic radiopaque markers comprise tantalum.

6. The method of claim 1 wherein the implantable medical device body comprises a tubular stent body including a plurality of struts.

7. The method of claim 6 wherein lightly electropolishing of the tubular stent body including the one or more attached radiopaque markers comprises:
   immersing the tubular stent body with one or more attached radiopaque markers into an electrolyte solution that is capable of electropolishing both the metal of the tubular stent body and the metal of the one or more attached radiopaque markers; and
   subjecting the immersed tubular stent body with the one or more attached radiopaque markers to an applied electrical current.

8. The method of claim 7 wherein the tubular stent body comprises nickel-titanium, the one or more attached radiopaque markers comprise tantalum, and the electrolyte solution comprises methanol and an acid selected from the group consisting of sulfuric acid, hydrochloric acid, and combinations thereof.

9. The method of claim 8 wherein the electrolyte solution is initially substantially void of water.

10. The method of claim 7 wherein the tubular stent body with the one or more attached radiopaque markers is immersed into the electrolyte solution for a period of time from about 10 seconds to about 1 minute while applying an electrical current density from about 400 amps/ft$^2$ to about 800 amps/ft$^2$ during light electropolishing.

11. The method of claim 10 wherein the tubular stent body with the one or more attached radiopaque markers is rotated periodically at an interval from about 5 seconds to about 20 seconds so that 1 or 2 rotations occur during the light electropolishing.

12. The method of claim 6 wherein primary electropolishing of the tubular stent body removes at least about 15 percent by weight of the tubular stent body.

13. The method of claim 6 wherein primary electropolishing of the tubular stent body removes from about 20 percent to about 30 percent by weight of the tubular stent body.

14. The method of claim 6 wherein the tubular stent body is immersed into the electrolyte solution before attachment of the one or more attached radiopaque markers for a period of time from about 30 seconds to about 4 minutes while applying an electrical current density from about 400 amps/ft$^2$ to about 800 amps/ft$^2$.

15. The method of claim 14 wherein the tubular stent body without any attached radiopaque markers is rotated periodically at an interval from about 5 seconds to about 20 seconds so that from about 6 to about 10 rotations occur during the primary electropolishing.

16. The method of claim 1 wherein lightly electropolishing the implantable medical device body with one or more attached radiopaque markers comprises:
   immersing the implantable medical device body including the one or more attached radiopaque markers into a first electrolyte solution that is capable of electropolishing the metal of the metallic implantable medical device body while subjecting the immersed implantable medical device body including the one or more attached radiopaque markers to an applied electrical current to electropolish the metallic implantable medical device body; and
   immersing the implantable medical device body including the one or more attached radiopaque markers into a second electrolyte solution different from the first electrolyte solution and that is capable of electropolishing the metal of the metallic radiopaque markers while subjecting the immersed implantable medical device body including the one or more attached radiopaque markers to an applied electrical current to electropolish the metallic one or more attached radiopaque markers.

17. The method of claim 16 wherein a cathode is positioned nearer the metal of the implantable medical device body than the metal of the one or more attached radiopaque markers during immersion in the first electrolytic solution.

18. The method of claim 16 wherein a cathode is positioned nearer the metal of the one or more attached radiopaque markers than the metal of the implantable medical device body during immersion in the second electrolytic solution.

19. A method of manufacturing and passivating a stent including one or more radiopaque markers, the method comprising:
- providing a metallic tubular stent body without any radiopaque markers attached thereto;
- primary electropolishing the metallic tubular stent body;
- attaching one or more metallic radiopaque markers to the tubular stent body, the one or more radiopaque markers comprising a metal that is different from that of the metallic tubular stent body; and
- lightly electropolishing the tubular stent body including the one or more attached radiopaque markers, the light electropolishing removing no more than about 5 percent by weight of the metallic tubular stent body with one or more attached radiopaque markers;
- wherein the light electropolishing of the metallic tubular stent body with the one or more attached radiopaque markers passivates an exterior surface of the metallic tubular stent body with the one or more attached radiopaque markers.

20. The method of claim 19 wherein the metallic tubular stent body is formed from sheet metal.

21. A method of manufacturing and passivating a stent including one or more radiopaque markers, the method comprising:
- providing a metallic tubular stent body without any radiopaque markers attached thereto:
- primary electropolishing the tubular stent body;
- attaching one or more metallic radiopaque markers to the tubular stent body, the one or more radiopaque markers comprising a metal that is different from that of the metallic tubular stent body; and
- lightly electropolishing the tubular stent body including the one or more attached radiopaque markers by immersing the tubular stent body with one or more attached radiopaque markers into an electrolyte solution that is capable of electropolishing both the metal of the metallic tubular stent body and the metal of the one or more attached radiopaque markers and subjecting the immersed tubular stent body with one or more attached radiopaque markers to an applied electrical current;
- wherein the light electropolishing removes no more than about 5 percent by weight of the tubular stent body with one or more attached radiopaque markers; and
- wherein the light electropolishing of the tubular stent body with the one or more attached radiopaque markers passivates an exterior surface of the tubular stent body with one or more attached radiopaque markers.

* * * * *